(12) United States Patent
Komvopoulos et al.

(10) Patent No.: US 8,927,283 B2
(45) Date of Patent: Jan. 6, 2015

(54) METHOD TO CONTROL CELL ADHESION AND GROWTH ON BIOPOLYMER SURFACES

(75) Inventors: Kyriakos Komvopoulos, Orinda, CA (US); Satomi Tajima, Beachwood, OH (US)

(73) Assignee: The Regents of the University of California, Oakland, CA (US)

( * ) Notice: Subject to any disclaimer, the term of this patent is extended or adjusted under 35 U.S.C. 154(b) by 1820 days.

(21) Appl. No.: 11/942,909

(22) Filed: Nov. 20, 2007

(65) Prior Publication Data

US 2009/0130164 A1    May 21, 2009

(51) Int. Cl.
*C12N 5/00* (2006.01)
*C08J 7/12* (2006.01)

(52) U.S. Cl.
CPC .............. *C08J 7/123* (2013.01); *C08J 2323/06* (2013.01)
USPC .......................................... 435/395; 435/402

(58) Field of Classification Search
USPC ................................................ 435/395, 402
See application file for complete search history.

(56) References Cited

U.S. PATENT DOCUMENTS

| | | | | |
|---|---|---|---|---|
| 5,246,451 | A | * | 9/1993 | Trescony et al. ............. 427/2.25 |
| 5,627,079 | A | * | 5/1997 | Gardella et al. .............. 436/525 |
| 5,804,263 | A | * | 9/1998 | Goldberg et al. ............ 428/34.7 |
| 2003/0040807 | A1 | | 2/2003 | Komvopoulos et al. |
| 2003/0113478 | A1 | | 6/2003 | Dang et al. |
| 2005/0214535 | A1 | | 9/2005 | Denes et al. |
| 2007/0014752 | A1 | | 1/2007 | Roy et al. |

OTHER PUBLICATIONS

U.S. Appl. No. 11/741,408.*
Bacakova, Lucie et al; "Adhesion and proliferation of cultured human aortic smooth muscle cells on polystyrene implanted with $N^+$, $F^+$ and $Ar^+$ ions: correlation with polymer surface polarity and carbonization"; 1996, *Biomaterials*, vol. 17, pp. 1121-1126.
Eberl, Thomas et al.; "Expermental In Vitro Endothelialization of Cardian Valve Leaflets"; 1992, *Ann Thorac Surg*, vol. 53, pp. 487-492.
Ertel, Sylvie I. et al.; "Radiofrequency plasma deposition of oxygen-containing films on polystyrene and poly(ethylene terephthalate) substrates improves endothelial cell growth"; 1990, *Journal of Biomedical Materials Research*, vol. 24, pp. 1637-1659.
Grinnell, Frederick et al.; "Adsorption characteristics of plasma fibronectin in relationship to biological activity"; 1981, *Journal of Biomedical Materials Research*, vol. 15, pp. 363-381.
Kottke-Marchant, K. et al.; "Human endothelial cell growth and coadulant function varies with respect to interfacial properties of polymeric substrates"; 1996, *Journal of Biomedical Materials Research*, vol. 30, pp. 209-220.
Lee, Jae-Suk et al.; "Selective adhesion and proliferation of cells on ion-implanted polymer domains"; 1993, *Biomaterials*, vol. 14, No. 12, pp. 958-960.

Ortenwall, Per et al; "Endothelial cell seeding reduces thrombogenicity of Dacron grarts in humans"; 1990, *J. Vasc Surg*, vol. 11, pp. 403-410.
Perego, Gabriele et al.; "Functionalization of poly-L-lactic-co-€ -caprolactone: effects of surface modification on endothelial cell proliferation and hemocompatibility"; 2003, *J. Biomater. Sc. Polymer Edn.*, vol. 14, No. 10, pp. 1057-1075.
Ramires, P.A. et al.; "Plasma-treated PET surfaces improve the biocompatibility of human endothelial cells"; 1998, *Department of Chemistry, University of Bari*, pp. 535-539.
Stansby, G. et al.; "Endothelial cell seeding of vascular grafts: status and prospects"; 1994, *Cardiovascular Surgery*, vol. 2 No. 5, pp. 543-546.
Sterpetti, Antonio V. et al.; "Endothelial Cell Seeding after Carotid Endarterectomy in a Canine Model Reduces Platelet Uptake"; 1992, *Eur J Vasc Surg*, vol. 6, pp. 390-394.
Tajima, S. et al., "Surface Modification of Low-Density Polyethylene by Inductively Coupled Argon Plasma"; 2005, *J. Phys. Chem, B.*, vol. 109, pp. 17623-17629.
Tajima, S. et al.; "Effect of ion energy fluence on the topography and wettability of low-density polyethylene exposed to inductively coupled argon plasma"; 2006, *J. Phys. D: Appl. Phys.*, vol. 39, pp. 1084-1094.
Williams, Stuart K.; "Endothelial Cell Transplantation"; 1995, *Cell Transplantation*, vol. 4, No. 4, pp. 401-410.
Williams, Stuart K. et al.; "Tissue-engineered vascular grafts"; 1996, *Nature Medicine*, vol. 2, No. 1, pp. 32-34.
Zinger, O. et al.; "Time-dependent morphology and adhesion of osteoblastic cells on titanium model surfaces featuring scale-resolved topography"; 2004, *Biomaterials*, vol. 25, pp. 2695-2711.
Klapperich C. et al.; "Chemical and Biological Characteristics of Low-temperature Plasma treated Ultra-high Molecular Weight Polyethylene for biomedical applications"; 2001, *Journal of Materials Science*, vol. 12, pp. 549-556.
PCT International Search Report for PCT/US2008/083090 dated May 29, 2009, 13 pages.

* cited by examiner

*Primary Examiner* — Ruth Davis
(74) *Attorney, Agent, or Firm* — Rudy J. Ng; Bret E. Field; Bozicevic, Field & Francis LLP

(57) ABSTRACT

Methods for treating surfaces of polymeric substrates (as used in medical implants) with inert plasmas to promote the growth of bioentities (such as cells) on these surfaces is disclosed. The treated surfaces are subsequently exposed to an environment to form functionalities associated with enhanced growth of the bioentity on the surface. For example, the substrate may be exposed to the ambient environment. The bioentity may then be deposited on the modified surface. This inert plasma treatment and exposure to a suitable environment does not degrade the implants, and thus improved implants are created. Also, due to the specific functional groups at the modified surface, high cell densities are achieved.

20 Claims, 12 Drawing Sheets

METHOD TO CONTROL CELL ADHESION AND GROWTH ON BIOPOLYMER SURFACES

STATEMENT AS TO RIGHTS TO INVENTIONS MADE UNDER FEDERALLY SPONSORED RESEARCH OR DEVELOPMENT

This invention was made with Government support under Grant (Contract) Nos. CMS-0528506 and CMS-0127754 awarded by the National Science Foundation. The Government has certain rights to this invention.

BACKGROUND OF THE INVENTION

Endothelial cell seeding is an effective method of preventing thromboembolism on surfaces of cardiovascular implants and biodevices because endothelial cells release chemical agents and proteins that block platelet adhesion and fibrin formation. Stansby, G. et al., *Cardiovasc Surg* 2:543-548 (1994); Eberl, T. et al., *Ann Thorac Surg* 53:487-492 (1992); Sterpetti, A. et al., *Eur J Vasc Surg* 6:390-394 (1992)). Seeding of vascular graft prosthesis with endothelial cells before implantation significantly increases graft patency and survival (Ortenwall, P. et al., *J Vasc Surg* 11:403-410 (1990); Meinhart, J. et al., *ASAIO J* 43:M515-M521 (1997)). The physicochemical characteristics of biomaterial surfaces may directly influence cell adhesion and spreading as well as signaling events that regulate a wide range of biological functions, such as cell growth and extracellular matrix synthesis (Ramires, P. A. et al., *Biomater* 23:397-406 (2002)). Since endothelial cells adhere poorly on hydrophobic polymer surfaces (Kottke-Marchant, K. et al. *J Biomed Mater Res* 30:209-220 (1996)), cell detachment from biopolymer surfaces may occur upon restoring blood circulation (Williams, S. K. et al., *Cell Transpl* 4:401-410 (1995)). To prevent thromboembolism, polymer surface treatment to enhance endothelial cell adhesion is essential prior to the device implantation.

Deposition of protein coatings and modification of the biochemical surface properties by energetic treatments are the most common methods of improving endothelial cell adhesion on polymer surfaces. Coating polymer surfaces with proteins, such as fibronectin (Pratt, K. J. et al., *J Biomed Mater Res* 23:1131-1147 (1989)) and collagen (Breithaupt-Faloppa, A. C. et al, *J Biomed Mater Res, Part B: Appl Biomater* 76B:49-55 (2006)), has been reported to promote cellular adhesion. Fibronectin enhances adhesion at cell boundaries, while collagen produces extracellular matrix contacts (Schakenraad, J. M. *Biomaterials science—An introduction to materials in medicine.* Eds. Ratner B D, Hoffman A S, Schoen F J, Lemons J E. San Diego, Calif.: Academic Press; p. 141-147 (1996)). However degradation of protein coatings is a limiting factor because it leads to cellular detachment (Grinnell, F. et al., *J Biol Chem* 257:4888-4893 (1982)) and, in turn, platelet adhesion.

Polymer surface modification by ion implantation and plasma treatment is another means of promoting cell adhesion. Protein adsorption and endothelial cell attachment, spreading, and proliferation are influenced by both chemical and physical properties of the polymer surface (Lee, J-S. et al., *Biomater* 14:958-960 (1993)). Endothelial cell proliferation and spreading can be enhanced by increasing the oxygen concentration at the polymer surface (Kottke-Marchant, K. et al. *J Biomed Mater Res* 30:209-220 (1996); Ertel, S. I. et al. *J Biomed Mater Res* 24:1637-1659 (1990)). Specifically, polar surface functionalities (e.g., carboxyl groups) promote cell adhesion (Perego, G. et al., *J Biomater Sci: Polymer Edn* 14:1057-1075 (2003)), while ion implantation, such as $Na^+$ (Lee, J-S. et al., *Biomater* 14:958-960 (1993)), $Ar^+$ (Pignataro, B. et al., *Biomater* 18:1461-1470 (1997)), and $F^+$ (Švorčík, V. et al., *J Mater Chem* 5:27-30 (1995)), increases the polymer surface polarity by oxygen incorporation. Surface modification by different plasma precursors including oxygen (Bačáková, L. et al., *Biomater* 17:1121-1126 (1996)), ammonia (Bačáková, L. et al., *Biomater* 17:1121-1126 (1996); Pu, F. R. et al. *Biomater* 23:2411-2428 (2002)) and air (Pratt, K. J. et al., *J Biomed Mater Res* 23:1131-1147 (1989)) can also promote endothelial cell adhesion on polymer surfaces due to the presence of polar surface functionalities. In contrast to ion implantation, plasma surface modification is confined within the outermost surface layer. However, a drawback with oxygen and air plasma treatments is the degradation of the material properties as a result of chain scission.

Therefore, it is desirable to have methods for growing cells on implants without degrading the implant, particularly when high cell densities are desired, and to have implants without degradation but with high cell densities.

BRIEF SUMMARY OF THE INVENTION

Accordingly, embodiments of the present invention utilize inert plasmas to treat surfaces of implants to promote the growth of bioentities (such as cells) on these surfaces. In one aspect, the treated surfaces are subsequently exposed to air to from oxygen functionalities on the surface, which are identified as promoting such growth. This inert plasma treatment and exposure to a suitable environment does not degrade the implants, and thus improved implants are created. In addition to the lack of degradation, high cell densities can be achieved.

In one embodiment, argon plasma is utilized. Argon plasma is a promising alternative to oxygen and air plasmas because it can improve the surface hydrophilicity (through the formation of oxygen surface functionalities upon the exposure of the reactive polymer surface to the ambient conditions) without affecting the bulk characteristics (Clouet, F. et al., *J Appl Polym Sci* 46:1955-1966 (1992); Tajima, S. et al., *J Phys Chem B* 109:17623-17629 (2005); Tajima, S. et al., *J. Phys. D: Appl. Phys.* 39: 1084-94 (2006)), each of which is incorporated by reference.

According to one exemplary embodiment, a polymeric substrate is treated with an inert plasma, thereby creating a modified surface on the polymeric substrate. The modified surface is exposed to an environment containing oxygen, thereby forming oxygen functionalities on the modified surface. Bioentities are then deposited onto the treated polymeric substrate.

According to another exemplary embodiment, an article comprises a polymeric substrate and bioentities on the polymeric substrate. The polymeric substrate comprises a modified surface and a bulk region. Oxygen functionalities are formed on the modified surface, and properties of the substrate are not degraded. In one aspect, the bioentities are cells, and a cell number density on the treated polymeric substrate is increased by at least 50% compared to a cell density on an untreated polymeric substrate. This increase is stable and is evident where an incubation period during depositing is equal to or greater than about 24 hours.

According to another exemplary embodiment, at least one family of functionalities associated with a growth of one or more bioentities on a polymeric substrate is identified. A polymeric substrate is treated with an inert plasma, thereby creating a modified surface on the polymeric substrate. The modified surface is exposed to an environment containing a basic constituent of the identified functionalities, thereby forming the identified functionalities on the modified surface. The bioentities are then deposited onto the treated polymeric substrate.

A better understanding of the nature and advantages of the present invention may be gained with reference to the following detailed description and the accompanying drawings.

DETAILED DESCRIPTION OF THE INVENTION

Figure 1:
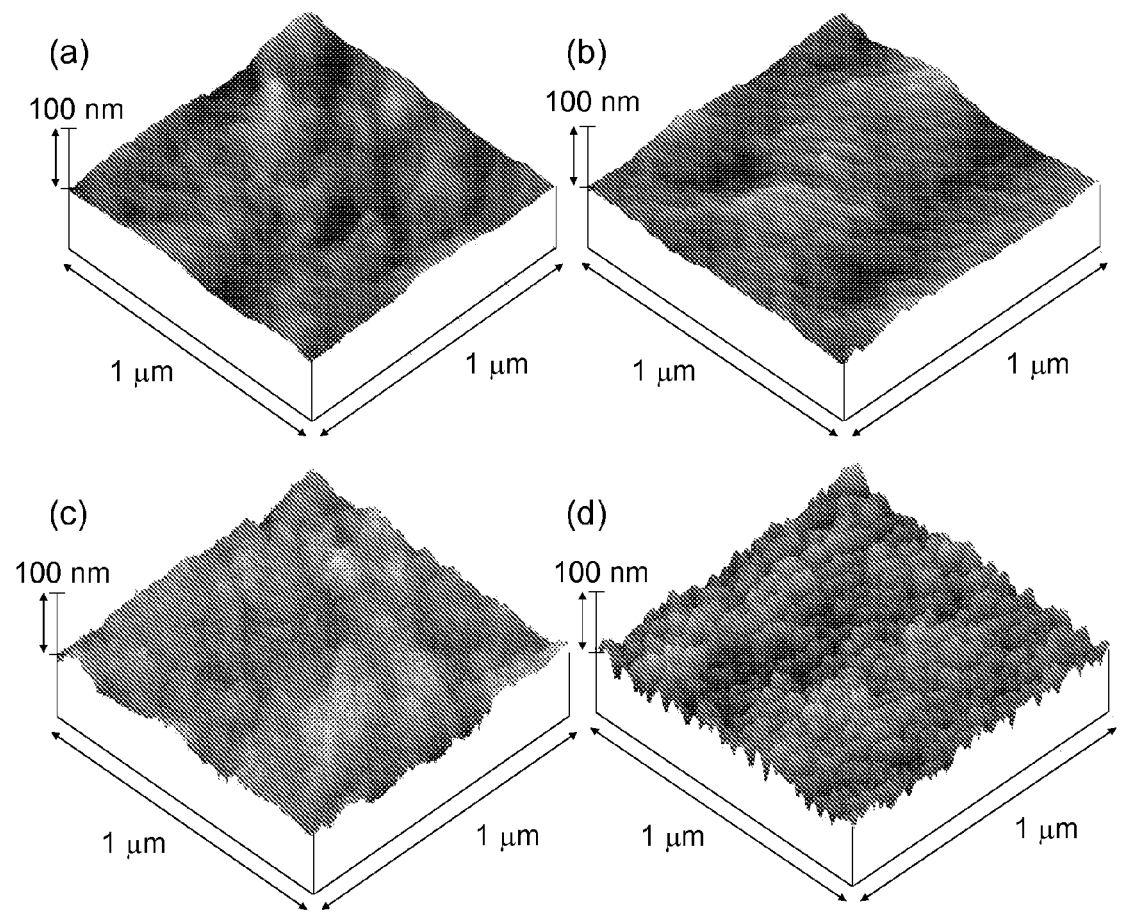
FIG. 1 shows surface topography images of LDPE for ion energy fluence equal to (a) 0 $J/m^2$ (untreated), (b) $2.8 \times 10^4$ $J/m^2$, (c) $1.8 \times 10^5$ $J/m^2$, and (d) $6.3 \times 10^5$ $J/m^2$.

Embodiments provide improved bioentity adhesion (e.g. for endothelial cells) and spreading on surfaces of polymeric substrates, such as low-density polyethylene (LDPE), without degrading the bulk properties of the substrate. In particular, high cell densities may be achieved due to the formation of oxygen functionalities at the substrate surface. The improved surfaces are created by treating the surfaces with inert plasma, which does not degrade the substrate and produces the desired surface functional groups. Simultaneous or subsequent to the treatment, the substrate is exposed to an environment containing a basic constituent (e.g. oxygen) to acquire a family of desired functional groups associated with the growth of the particular bioentity that is to be deposited (or seeded) on the surface. As shown herein, different oxygen functionalities are produced on LDPE surfaces by variation of the plasma process parameters.

The bioentity is then deposited on the resulting modified surface. The response of endothelial cells seeded on untreated and plasma-treated LDPE surfaces is quantified in terms of the density of the adhered cells, cell spreading behavior, and cytoskeleton morphology. The adhesion of cells seeded on plasma-treated LDPE surfaces possessing different morphologies, hydrophilicity levels, and surface chemical functionalities are shown to last for relatively short and long incubation periods.

As used herein, the term "bioentities" includes cells, proteins, viruses and other substances that are living organisms or extracted from living organisms. As used herein, the term "biomaterial" refers to non-reactive materials that are generally tolerated in the body. As used herein, the term "functionalities" refers to certain type or family of functional groups that can be related to each other. In some embodiments, functionalities may contain a basic constituent portion (such as an oxygen atom). Examples of functionalities include carboxyls, carbonyls, aldehydes, etc.

Any suitable polymeric substrate may be used in embodiments of the invention. The substrate may be a layer on a larger surface, or may be a stand-alone substrate that may be in any suitable form. For example, the substrate may be in the form of a plate, a tube, sphere, or complex shape. In preferred embodiments, the substrate is in the form of a tube so that the formed article can be used as an artificial artery, catheter, or the like. The substrate may also have a convex shape, a concave shape, a solid of revolution shape, or any other suitable shape.

The substrate material may comprise any suitable polymers including homopolymers, copolymers, blends, etc. Examples of suitable polymeric materials include polyethylene, medium-density polyethylene, low-density polyethylene, linear low-density polyethylene, polymethylmethacrylate, silicones, and polyurethanes. In some embodiments, high-molecular-weight polymers such as those that can be used in orthopedic implants or medical devices can be present in the substrate.

Once obtained, the polymeric substrate is treated with an inert gas plasma (such as argon and helium), via any suitable plasma technique. In some embodiments, the polymeric substrate may be exposed to an inductively coupled plasma to modify the surface of the polymeric substrate. An inductively coupled plasma is a plasma that is driven by a current oscillating in a coil, either around or adjacent to the vacuum vessel. The oscillating current gives rise to a time-varying magnetic field in the gas, which induces a local electric field, which accelerates electrons and excites the plasma. In another embodiment, a capacitively coupled plasma (CCP) process is used.

The treatment with an inert plasma (e.g., Ar and He) can be used to create free dangling bonds at the polymer surface as produced from the ion and/or radical bombardment. The modification of the surface of the polymeric substrate could also be mechanical in nature. For example, the modified surface of the polymeric substrate can be rougher than an untreated polymeric substrate.

The inductively coupled plasma process may have any suitable process parameters. For example, in some cases, the plasma chamber may be kept between about 50 and about 800 mTorr (e.g., 500 mTorr), the plasma power may be between about 75 and about 1200 Watts (e.g., 1200 W), the sample distance may be varied (e.g. between about 0 cm and about 58 cm) and the treatment time may be between about 1 minute and about 30 minutes (e.g., about 15 minutes).

This plasma treatment advantageously does not cause chain scission in the substrate or other degradation of the properties of the substrate, including the surface and bulk properties. In contrast, as mentioned above, ion implantation can affect the substrate properties within a significant depth from the substrate surface, which may cause it to not function as desired. Also, other plasma treatments also cause degradation in properties, such as tensile strength, color, shape, etc, in the surface and/or the bulk properties. Whereas, the inert plasma provide nanotexturing of the surface, but the mechanical and physical properties are preserved.

Generally, plasma treatments of a polymeric substrate can be achieved by placing the workpiece in contact with the gas to be used in the treatment and imposing high-energy radiation, sufficient to ionize the gas to a plasma state. While not intending to be bound by any particular theory or mechanism of operation, it is believed that the plasma activates the polymer chains that are in contact with the plasma by dissociating covalent bonds in the polymer chains. The reactions that then occur at these activated sites will vary with the operating conditions such as the power density, exposure time, working pressure, gas flow rate, temperature, electrode spacing, chamber dimensions, substrate bias voltage, or combinations of these conditions.

Figure 11:
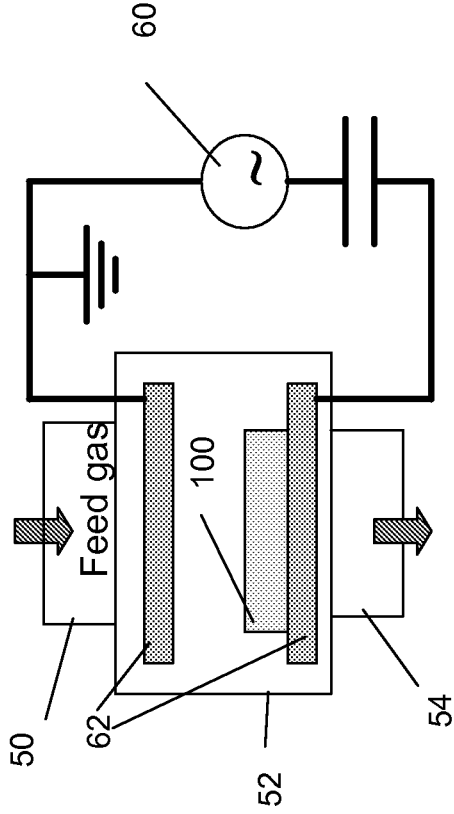
FIG. 11 shows a schematic illustration of a capacitively coupled plasma apparatus.

In a capacitively coupled plasma (CCP) process, electrodes are placed inside a plasma processing chamber, and they ionize precursor gases to form a plasma. An example of a capacitively coupled plasma processing apparatus is shown in FIG. 11. FIG. 11 shows a chamber 52 with an inlet port 50 and a downstream outlet port 54. Electrodes 62 are within the chamber, and are operatively coupled to an rf power source 60. A sample 100 (e.g., the previously described substrate) may rest on one of the electrodes 62. As a feed gas is introduced into the chamber 52, the gas is ionized by the electrodes 62. The ionized gas and neutral atoms or molecules may thereafter interact with the sample 100.

Figure 12:
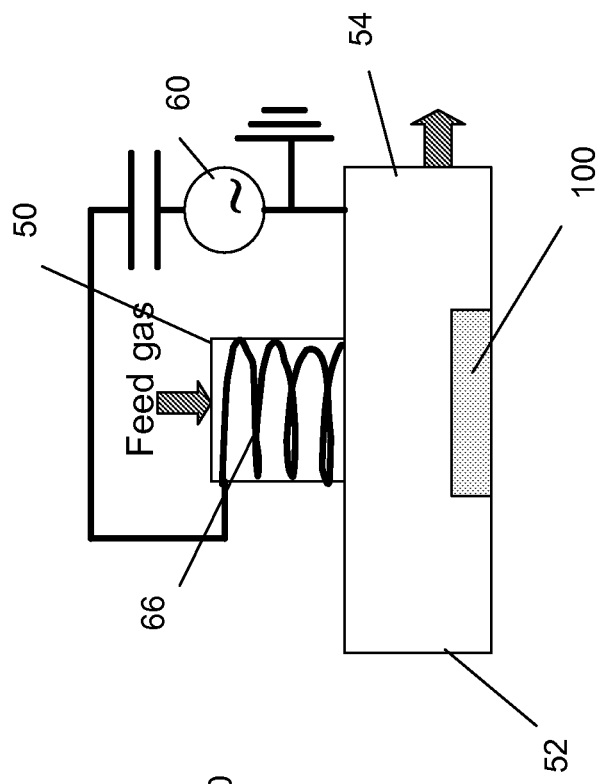
FIG. 12 shows a schematic illustration of an inductively coupled plasma apparatus.

An inductively coupled plasma (ICP) may also be used. FIG. 12 shows a schematic view of an inductively coupled plasma processing apparatus. It includes a chamber 52 and a sample 100 in the chamber 52. The chamber includes an inlet 50 and an outlet 54. A coil 66 is proximate to the inlet 50 and is electrically coupled to an rf power source 60. The feed gas is introduced into the chamber 52 via the inlet 50, and when it is introduced, it is ionized by the coil 66 and the ionized gases pass into the chamber 52 and interact with sample 100.

In some embodiments, a shield may be used to shield the polymeric substrate from the plasma to control the plasma process and to selectively modify the surface (either physically and/or chemically) of the polymeric substrate. The advantage of using a shielded plasma over pulsed or downstream plasma is that the treatment conditions can be varied without changing the power supply or chamber configuration. The shield may comprise inorganic materials such as Al, Pyrex®, LiF, $CaF_2$, $Al_2O_3$, and $SiO_2$. By using a shield, one can control the types of plasma species and/or radiation reaching the polymeric substrate. For example, Al and other radiation blocking metals may only allow uncharged particles to reach the polymer substrate. On the other hand, LiF, $CaF_2$, $Al_2O_3$, and $SiO_2$ may allow only uncharged particles, UV (ultraviolet) and/or VUV (vacuum ultraviolet radiation) to reach the polymer substrate.

The shield may be stationary within the chamber, or is preferably movable (e.g., coupled to a movable motor) in the chamber so that it can cover or not cover some or all of the polymeric substrate during the surface modification process step.

Schematic illustrations of various processing chambers with shields are shown in FIGS. 13(a)-13(d). The shields shown in FIGS. 13(a)-13(d) and other types of shields can be used in the apparatuses shown in FIGS. 11 and 12. Shields can be used in both inductively or capacitively coupled plasma processes, or not at all.

Figures 13A, 13B:
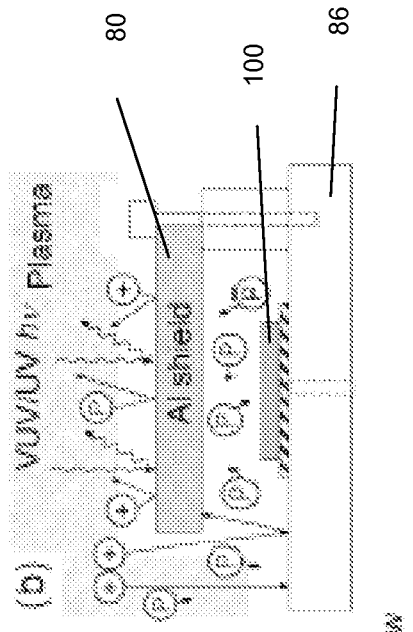
FIGS. 13(a)-13(d) shows schematic illustrations of inductively coupled plasma chambers with shields of different cut-off wavelength number.

FIG. 13(a) shows a crystal shield apparatus including a crystal shield 80 and a holder that may or may not be able to move the crystal shield. The shield covers a sample 100 on a sample holder 86 and helps to prevent ionized particles (+) from reaching the sample 100. Neutral particles (P) and UV/VUV radiation can reach the sample 100 through a space that is between the sample holder 86 and the shield 80 (e.g., by a side passage via diffusion).

FIG. 13(b) shows an aluminum shield apparatus including an aluminum shield 80 and a holder that may or may not be able to move the aluminum shield. The shield covers a sample 100 on a sample holder 86 and helps to prevent ionized particles (+) and VUV/UV radiation from reaching the sample 100. Neutral particles (P) can reach the sample 100 through a space that is between the sample holder 86 and the shield 80 (e.g., by a side passage via diffusion).

Figures 13C, 13D:
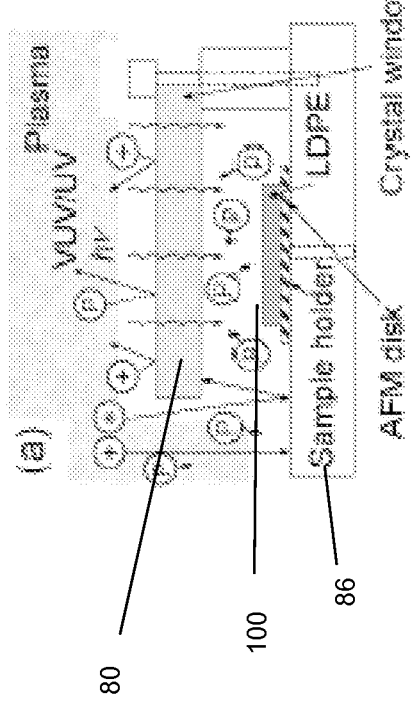

FIG. 13(c) shows a LiF shield apparatus including a LiF shield 80, and a holder in the form of an o-ring. The shield covers a sample 100 on a sample holder 86 and it helps to prevent ionized (+) and neutral (P) particles from reaching the sample 100. Only UV/VUV radiation can reach the sample 100.

FIG. 13(d) shows a polymer shield apparatus including a Pyrex® shield 80 and a holder. The shield covers a sample 100 on a sample holder 86 and helps to prevent ionized (+) and neutral (P) particles, as well as VUV radiation from reaching the sample 100. Only UV radiation can reach the sample 100.

As illustrated in FIGS. 13(a)-13(d), by using a shield, the properties of the sample 100 can be selectively altered without modifying processing conditions such as power, gas flow rate, etc. during a plasma process.

In one embodiment, after the plasma treatment, the modified surface is exposed to an environment containing oxygen. For example, the modified surface can be exposed to ambient conditions (i.e. air with room temperature and pressure), which contains oxygen. The exposure to the oxygen environment causes oxygen functionalities to form on the modified surface. In one aspect, upon exposure to the ambient, the free dangling bonds at the polymer surface produced from the $Ar^+$ ion and/or radical bombardment are saturated by oxygen from the atmosphere. High oxygen content is desirable for cell attachment and hydrophilicity enhancement.

Figure 3:
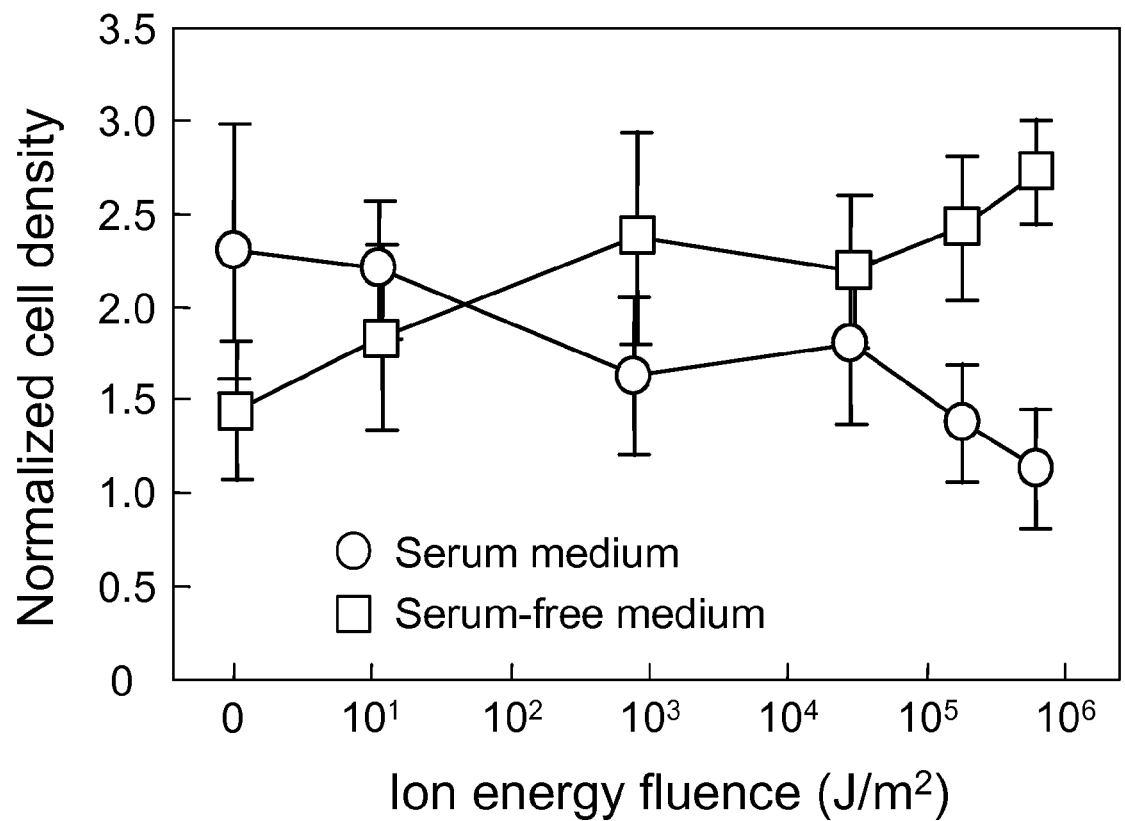
FIG. 3 shows a graph of normalized density of cells adhered on LDPE surfaces in (○) serum and (□) serum-free medium. The cells were seeded in each medium and incubated for 3 h. The cell density was normalized by the number of seeded cells.
Figure 6:
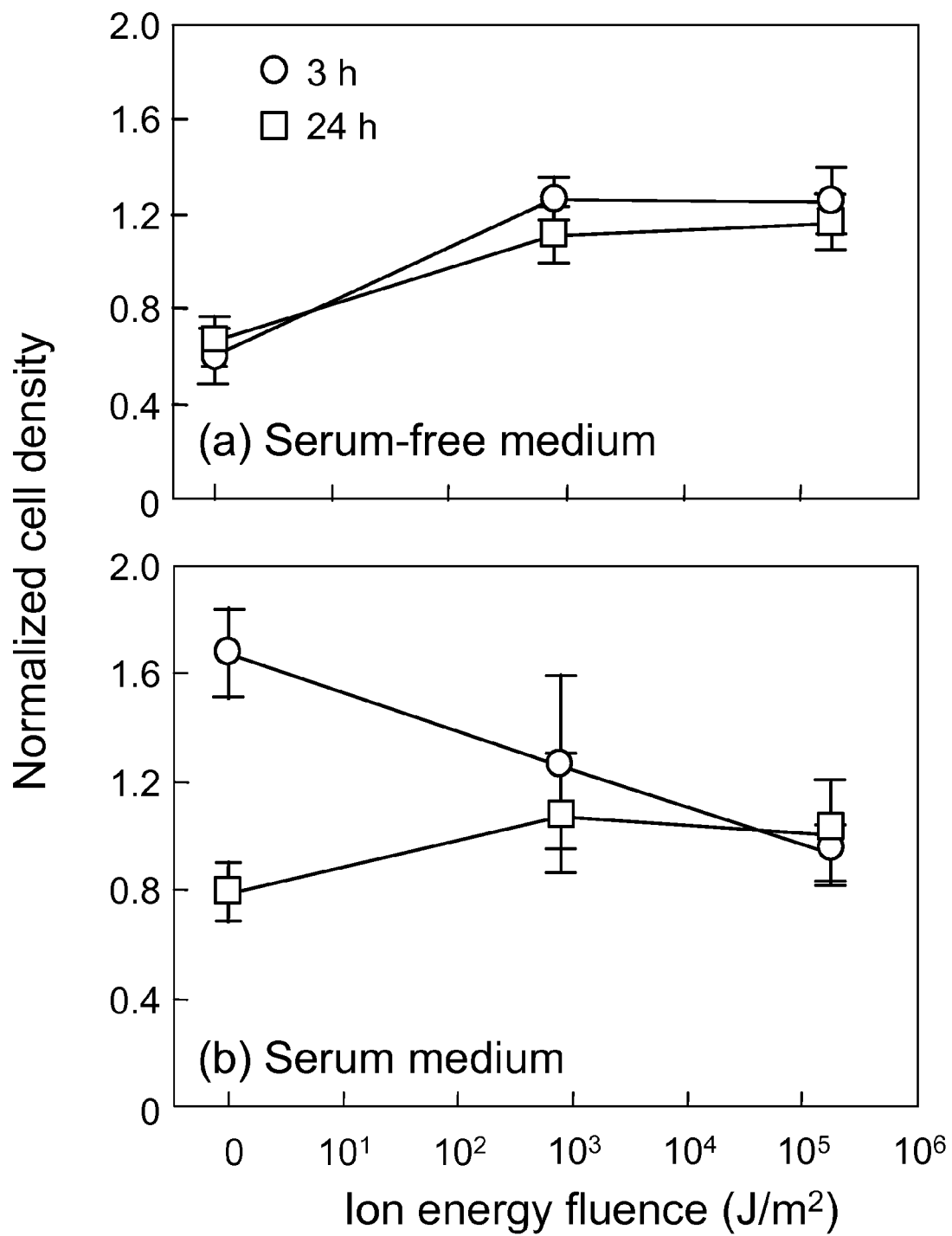
FIG. 6 shows a graph of normalized density of cells adhered on LDPE surfaces in (a) serum-free medium and (b) serum medium. The cells were seeded in each medium and incubated for 3 h (○) and 24 h (□). The cell density was normalized by the number of seeded cells.
Figure 9:
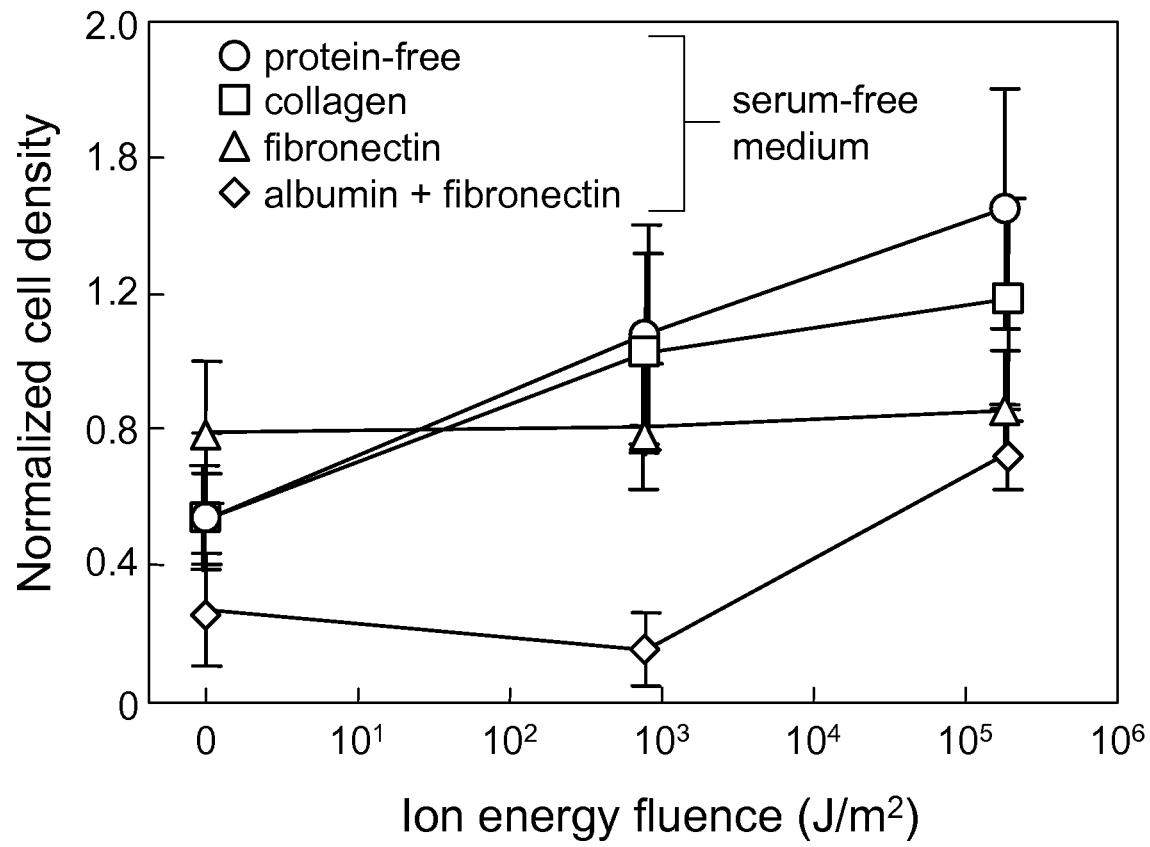
FIG. 9 shows a graph of normalized density of cells adhered on LDPE surfaces. Different proteins were pre-adsorbed on the polymer surfaces prior to cell seeding: (○) no proteins, (□) collagen, (△) fibronectin, and (◇) BSA/fibronectin mixture. The cells were seeded in serum-free medium and incubated for 3 h. The cell density was normalized by the number of seeded cells.

One or more bioentities, such as endothelial cells and/or proteins, are then deposited on the modified surface having the oxygen functionalities. In one embodiment, as described herein, the substrate is put into a Petri dish containing the bioentities and incubated for a set period of time, e.g. 3 or 24 hours. As shown in FIGS. 3, 6, and 9, the achieved cell density on the substrate can be increased significantly. In particular, since the surface is not degraded the cell density also does not degrade.

In the examples shown below, the cell density can be increased by at least 50% compared to a cell density on an untreated polymeric substrate. Note that for these examples, the normalized cell density equals the number of cells attached onto the polymer surface after incubation and staining divided by the number of cells seeded initially (i.e. before incubation). This increased cell density can be maintained over time as exhibited by the increase in FIG. 6 lasting even after incubation equal to or greater than about 24 hours.

In one embodiment, a cell number density on the treated polymeric substrate is at least 80% of an initial cell number density in a sample of the cells used in the depositing step. In another embodiment, a cell number density on the treated polymeric substrate is greater than an initial cell number density in a sample of the cells used in the depositing step.

In one embodiment, a single type of bioentity is deposited on the substrate. For example, a serum containing various proteins, such as fibronectin, collagen, albumin, etc., which closely represents human blood, is not deposited prior to the deposition of endothelial cells.

In one embodiment, the substrate is a biomaterial that is used as an implant for medical treatment. For example, the implant may be a prosthetic that is to be placed in the knee or an artificial artery. In both instances, the implant biocompatibility can be improved by the deposition of bioentities on the implant. The knee prosthetic can provide increased mobility and the artificial artery can have a reduced chance of thromboembolism.

In other embodiments, functionalities besides oxygen may be employed. Accordingly, in one aspect, at least one family of functionalities associated with a growth of one or more bioentities on a polymeric substrate are identified. This may be done experimentally or determined from known biochemical relationships between a bioentity and a particular constituent of a chemical group or family. The modified surface would then be exposed to an environment containing that chemical group or family. Thus, the identified functionalities are formed on the modified surface. A film of the bioentities is then deposited onto the treated polymeric substrate.

Additionally, one or more levels of an amount of the identified functionalities for enhancement of the deposition of the bioentities on the polymeric substrate can be identified. That is to say a critical amount of the functionalities may be determined. Parameters that provide at least one of the levels of functionalities can then be determined. In one embodiment, the parameters include a plasma power and a distance from a plasma source and the polymeric substrate.

EXAMPLES

Experimental Procedures

Materials and Plasma Surface Modification.

Pellets of LDPE (Sigma-Aldrich, St. Louis, Mo.) were pressed against glass slides to obtain samples of 1 cm in diameter and thickness in the range of 800-900 μm. The details of the sample fabrication procedure have been presented elsewhere (Tajima, S. et al., *J Phys Chem B* 109: 17623-17629 (2005)). X-ray diffraction and differential scanning calorimetry showed that the crystallinity of the LDPE samples was ~50%. A radio frequency (rf) inductively coupled plasma source (Litmas, Charlotte, N.C.) comprising a hollow ceramic tube with a winded helical coil was used to modify (both physically and chemically) the sample surfaces with Ar plasma and, thus, produce LDPE surfaces of different hydrophilicity (wettability) and oxygen surface functionalities. A high-purity (99.999%) Ar gas (Praxair, Danbury, Conn.) was introduced into the vacuum chamber at a flow rate of 100 sccm, while the working pressure was maintained at 500 mTorr during the treatment. To obtain different surface modifications, the plasma power and the sample distance from the power source were varied to yield ion energy fluences (measured with a Langmuir probe) as high as $6.3 \times 10^5$ $J/m^2$ (Tajima, S. et al., *J Phys Chem B* 109:17623-17629 (2005); Tajima, S. et al., *J Phys D: Appl Phys* 39:1084-1094 (2006)). The roughness and wettability of both untreated and plasma-treated LDPE surfaces were determined from atomic force microscopy and goniometry measurements (Tajima, S. et al., *J Phys Chem B* 109:17623-17629 (2005); Tajima, S. et al., *J Phys D: Appl Phys* 39:1084-1094 (2006)). Oxygen concentrations and amounts of oxygen functionalities were calculated from X-ray photoelectron spectroscopy (XPS) spectra. The good agreement between more than 25 contact angle measurements and 15 XPS spectra obtained from untreated LDPE surfaces confirmed the robustness of the sample preparation procedure. The roughness and carbon-oxygen surface functionalities of both untreated and plasma-treated LDPE surfaces are given in Table 1 in terms of plasma treatment conditions. The zero sample distance implies that the LDPE sample was centered at the bottom of the plasma source inside the ceramic tube without touching the tube wall. Six measurements of the ion energy fluence at zero sample distance obtained with a Langmuir probe placed at this position revealed insignificant differences.

TABLE 1

Effect of treatment conditions on surface roughness and concentration of oxygen and carbon-oxygen functionalities.

| Treatment conditions (power, sample distance) | Ion energy fluence ($J/m^2$) | Surface roughness* $R_q$ (nm) | Oxygen (at %) | Carbon-oxygen functionalities (at %) | | | | |
|---|---|---|---|---|---|---|---|---|
| | | | | C—C C—H | $C^\beta$ | C—O | C=O O—C—O | O=C—OH O=C—O |
| Untreated | 0 | 3.3 ± 0.5 | 1.1 | 100 | 0 | 0 | 0 | 0 |
| 225 W, 58 cm | $(1.1 \pm 0.3) \times 10^1$ | 4.3 ± 0.4 | 1.5 | 81.4 | 18.6 | 0 | 0 | 0 |
| 375 W, 58 cm | $(7.8 \pm 1.1) \times 10^2$ | 4.3 ± 0.4 | 2.7 | 69.3 | 27.2 | 3.5 | 0 | 0 |
| 1200 W, 58 cm | $(2.8 \pm 0.5) \times 10^4$ | 5.2 ± 0.9 | 13 | 49.6 | 31.4 | 12.2 | 4.3 | 2.5 |
| 1200 W, 15 cm | $(1.8 \pm 0.1) \times 10^5$ | 5.7 ± 1.0 | 20 | 37.1 | 28.3 | 15.6 | 11.8 | 7.2 |
| 1200 W, ~0 cm | $(6.3 \pm 0.4) \times 10^5$ | 10.8 ± 0.8 | 37 | 40.7 | 25.7 | 11.1 | 14.3 | 8.2 |

*Calculated from 1 μm² scan area images.

In embodiments of the invention, the plasma power is between 1000 and 1300 W (e.g. 1200 W) and the sample distance is between 0-60 cm. In some embodiments, the surface roughness is above 4.3 nm (e.g. between 5.2 nm-11 nm). Also, the atomic percentage of oxygen may be above 2.7% and preferably above 10%. Ranges in embodiments may be supported by tables and graphs herein. For example, the surface roughness may be above 5.5 nm and the atomic percentage of oxygen above 20%.

Endothelial Cell Culture.

Bovine aortic endothelial cells (BAECs) were isolated and characterized as described previously (Moon, J. J. et al., *J Cellul Physiol* 203; 166-176 (2005)). BAECs were cultured in Dulbecco's modified Eagle's medium (DMEM) supplemented with 10% fetal bovine serum (FBS), 2 mM L-glutamine, 1 mM of penicillin-streptomycin, and 1 mM of sodium pyruvate (serum medium) (all obtained from Gibco-BRL, Grand Island, N.Y.). Endothelial cell cultures were maintained in a humidified 95% air—5% $CO_2$ incubator at 37° C. All experiments used cultures between passage 6 and passage 13.

Endothelial Cell Seeding.

Untreated and plasma-treated LDPE samples that were adhered on glass slides by double-sided tape were fixed at the bottom of a square Petri dish of 82.8 $cm^2$ surface area. Cell detachment from the tissue culture dish was accomplished by trypsinisation, terminated after 3 min by diluting with serum medium. Subsequently, the cells were isolated from the enriched DMEM by centrifugation (performed at 1200 rpm for 3 min) followed by the addition of fresh medium with or without serum. The number of seeded cells was determined with a hemocytometer. An amount of 1 mL of medium with BAECs was seeded on the LDPE surface. Petri dishes containing cells were incubated for 3 or 24 h to allow cell adhesion and spreading to occur. After cell incubation, the medium was gently aspirated and rinsed with phosphate buffered saline (PBS) to remove any non-adherent cells. Then the cells were fixed in 4% paraformaldehyde (Fisher Scientific, Pittsburgh, Pa.) for 15 min and permeabilized with 0.5% Trition X-100 (EM Chemicals, Gibbstown, N.J.) for 5 min.

To compare the effects of different adsorbed proteins on cell adhesion, four different plasma and matrix proteins were pre-adsorbed on the LDPE surfaces: (a) bovine serum albumin (BSA) (Sigma-Aldrich, St. Louis, Mo.), (b) collagen type I from rat tail (BD Biosciences, San Jose, Calif.), (c) fibronectin from bovine plasma (Sigma-Aldrich, St. Louis, Mo.), and (d) a mixture of fibronectin and BSA. These proteins were allowed to adsorb on the sample surfaces 1 h prior to the cell seeding. 5 $\mu g/cm^2$ of collagen and an equal amount of fibronectin were pre-adsorbed on the sample surfaces. The diluting medium of collagen and fibronectin consisted of 0.1% acetic acid and PBS of pH 7.4 (Sigma-Aldrich, St. Louis, Mo.), respectively. In addition to the four individual proteins, a mixture of 1% BSA and 5 $\mu g/cm^2$ fibronectin were also pre-adsorbed on the sample surfaces. The addition of albumin in fibronectin has been reported to change the packing arrangement of the fibronectin molecules, which, in turn, activates the cells to adhere on a hydrophobic surface (Grinnell, F. et al., *J Biol Chem* 257:4888-4893 (1982); Grinnell, F. et al., *J Biomed Mater Res* 15:363-381 (1981)). Before cell seeding, excess proteins were rinsed twice with PBS. The cells were seeded in serum-free medium and incubated for 3 h.

Endothelial Cell Staining and Imaging.

Fluorescein isothiocyanate-phalloidin (Invitrogen, Carlsbad, Calif.) was used to stain actin filaments in the cells for 1 h in the dark, followed by three 5-min PBS rinses. For cell counting, the cell nuclei were stained with 300 nM of 4',6-diamidino-2-phenylindole (DAPI) (Invitrogen, Carlsbad, Calif.) for 5 min, followed by three 5-min PBS rinses. After rinsing with PBS, a Vector-Shield antifade solution (Vector Laboratories, Burlingame, Calif.) was applied to the LDPE surface for fluorescence microscopy measurements. Cell imaging was performed with an inverted fluorescence microscope (TE 300, Nikon, Melville, N.Y.) equipped with a high-speed digital camera imaging system (Compix, Sewickley, Pa.). A 10× magnification and a field size of 0.55 $mm^2$ were used to count the nuclei of the cells adhered on the LDPE surfaces, while a 40× magnification and a field size of 0.04 $mm^2$ were used to observe the cytoskeleton morphologies and study the actin filament evolution. At least three random visual fields were obtained from each sample.

Statistical Analysis.

The results are expressed as mean and standard deviation values. For cell counting, nine measurements were obtained from three samples treated identically. Differences in the results of the untreated and the plasma-treated LDPE samples were evaluated by performing a variance analysis using Holm's t-test (Glantz, S. A. *Primer of Biostatistics* 6th edition. San Francisco, Calif.: McGraw-Hill; Chapters 3 and 4 (2005)). The results for serum and serum-free media and LDPE surfaces with and without pre-adsorbed proteins were compared with unpaired Student's t-test. Statistical significance was considered for a p value of less than 0.05.

Results And Discussion

Plasma-Induced Surface Modification of Polyethylene.

FIG. 1 shows the effect of ion energy fluence on the surface topography of LDPE. Corresponding root-mean-square roughness $R_q$ values (measured from 1 $\mu m^2$ area scans) are given in Table 1 in terms of plasma treatment conditions. Increasing the ion energy fluence up to ~1.0×10$^5$ J/m$^2$ resulted in mild surface roughening. However, significantly rougher surfaces were produced for ion energy fluence of 6.3×10$^5$ J/m$^2$. The topography of the plasma-treated surfaces for ion energy fluence up to 7.8×10$^2$ J/m$^2$ was almost identical to that of the untreated surface (FIG. 1(a)). Nanoscopic surface features were observed for ion energy fluence on the order of 10$^4$ J/m$^2$ or higher (FIGS. 1(b) and 1(c)). In addition, nanometer-sized asperities were produced when the ion energy fluence was increased to 6.3×10$^5$ J/m$^2$ (FIG. 1(d)). The results presented in Table 1 and FIG. 1 indicate that variation of the ion energy fluence by several orders of magnitude resulted in nanoscale modification of the surface morphology.

Figure 2:
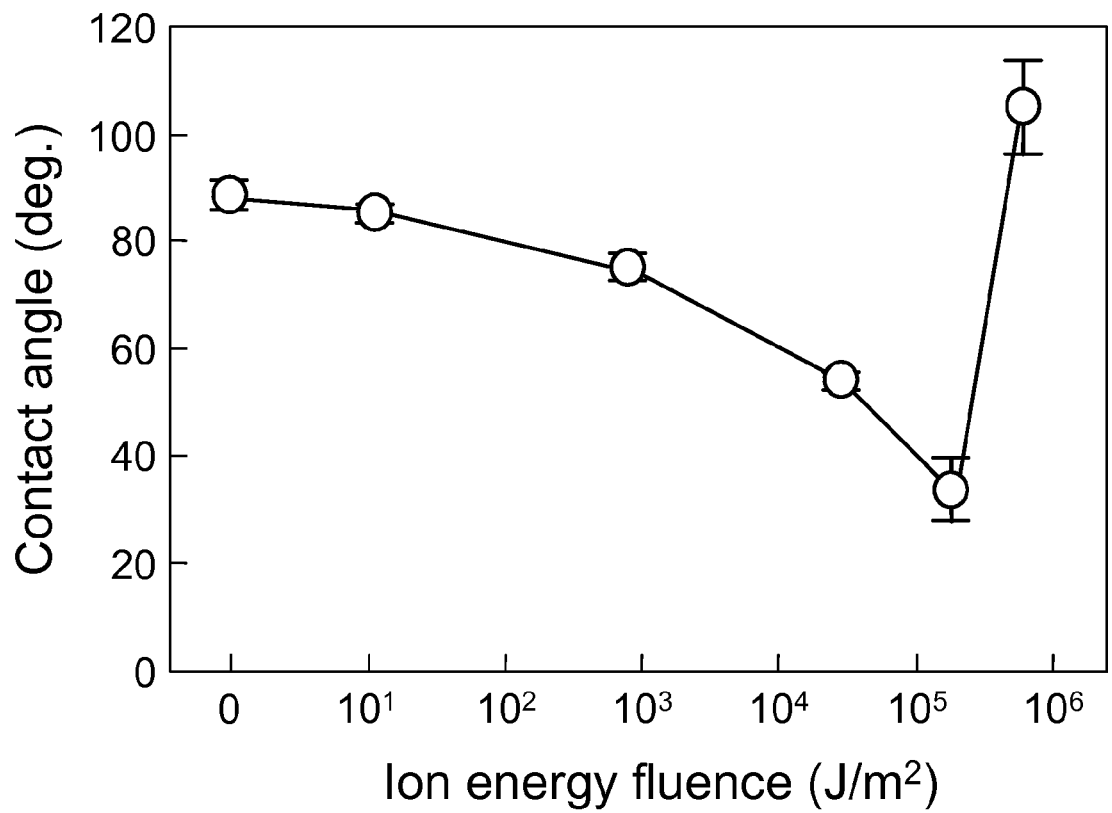
FIG. 2 shows a graph of contact angle versus ion energy fluence.

FIG. 2 provides insight into the effect of ion energy fluence on the surface wettability. The contact angle decreased continuously with the increase of the ion energy fluence up to 1.8×10$^5$ J/m$^2$; however, an abrupt increase in the contact angle was encountered when the ion energy fluence was increased to 6.3×10$^5$ J/m$^2$. This trend is attributed to the effect of nanoscale asperities (FIG. 1(d)) and has been investigated in detail in a previous study (Tajima, S. et al., *J Phys D: Appl Phys* 39:1084-1094 (2006)). The data shown in FIG. 2 reveal a strong effect of the plasma treatment conditions on the polymer surface hydrophilicity.

In addition to the nanotopography and wettability modifications, the formation of different surface oxygen functionalities also showed a dependence on the ion energy fluence (Table 1). Small amounts of carbon-oxygen functionalities were found on the LDPE surfaces subjected to relatively low ion energy fluence (7.8×10$^2$ J/m$^2$), whereas carbonyl (C=O) and carboxyl (O=C—OH) groups were detected on the LDPE surfaces exposed to ion energy fluence above 2.8×10$^4$ J/m$^2$. Thus, LDPE surfaces exhibiting different nanoscale morphologies, hydrophilicity levels, and surface chemistries were obtained by varying the ion energy fluence during the Ar plasma treatment.

Effect of Plasma-Induced Surface Modification on Cell Adhesion and Spreading.

FIG. 3 shows the normalized density of the cells adhered on LDPE surfaces after incubation for 3 h in serum-free and serum media as a function of ion energy fluence. In this figure and subsequent similar figures, data for zero ion energy fluence correspond to untreated LDPE. Normalized density is obtained by dividing the cell density for a given treatment (e.g. ion energy fluence and distance) by an initial cell density in a sample of the cells used in the depositing step, e.g. of the Petri dish before incubation. Thus, in one embodiment, normalized cell density equals the number of cells attached onto the polymer surface after incubation and staining divided by the number of cells seeded initially (i.e. before incubation).

While the cell density in serum-free medium increased with the ion energy fluence, an opposite trend was obtained in serum medium. Despite differences in the nanotopography for ion energy fluence equal to 1.8 and $6.3 \times 10^5$ J/m² (Table 1; p=0.00), changes in cell adhesion (FIG. 3) are not statistically discernible in both serum (p=0.125) and serum-free (p=0.08) media. Even though the contact angle measurements were affected by the formation of nanoscopic asperities on the LDPE surfaces treated with ion energy fluence of $6.3 \times 10^5$ J/m² (FIGS. 1(d) and 2), for a given medium, the cell density was similar to that of the LDPE surface treated with ion energy fluence of $1.8 \times 10^5$ J/m² which did not produce nanoscale asperities (FIG. 1(c)). This finding is in agreement with a previous study where the nanoscale topography effect on the cell adhesion and growth characteristics was found to be secondary (Zinger, O. et al., *Biomater* 25:2695-2711 (2004)). However, for ion energy fluence equal to 1.8 and $6.3 \times 10^5$ J/m², cell adhesion in the serum medium was significantly less than in the serum-free medium, suggesting that some serum proteins (e.g., BSA) may bind to the surfaces and block cell-surface interactions.

Unlike earlier studies that investigated the interdependence of cell adhesion and oxygen functionalities resulting from different plasma precursors (Ertel, S. I. et al. *J Biomed Mater Res* 24:1637-1659 (1990)) or ion implantation at different energy levels (Pignataro, B. et al., *Biomater* 18:1461-1470 (1997)), FIG. 3 shows that the density of the cells adhered on the plasma-treated LDPE surfaces was not affected significantly by the presence of different oxygen functionalities and/or nanoscale asperities for ion energy fluence less than $6.3 \times 10^5$ J/m². Although plasma treatment promoted cell adhesion in the serum-free medium, the density of the adhered cells was not influenced by the modification of the nanoscale morphology and the surface chemistry. In addition, cell adhesion in the serum medium exhibited a completely different trend from that in the serum-free medium. This phenomenon has not been observed in previous studies where the cells were reported to adhere on hydrophilic surfaces both in serum and serum-free media (Ertel, S. I. et al. *J Biomed Mater Res* 24:1637-1659 (1990)). It is believed that the serum proteins quickly adsorbed on the polymer surface before cell adhesion. These proteins might modify the plasma-treated hydrophilic surfaces or exhibit different protein conformations (Grinnell, F. et al., *J Biol Chem* 257:4888-4893 (1982)) on both untreated and plasma-treated LDPE surfaces during the 3 h incubation period, resulting in positive or negative effects on the cell adhesion and spreading behavior.

Figure 4:
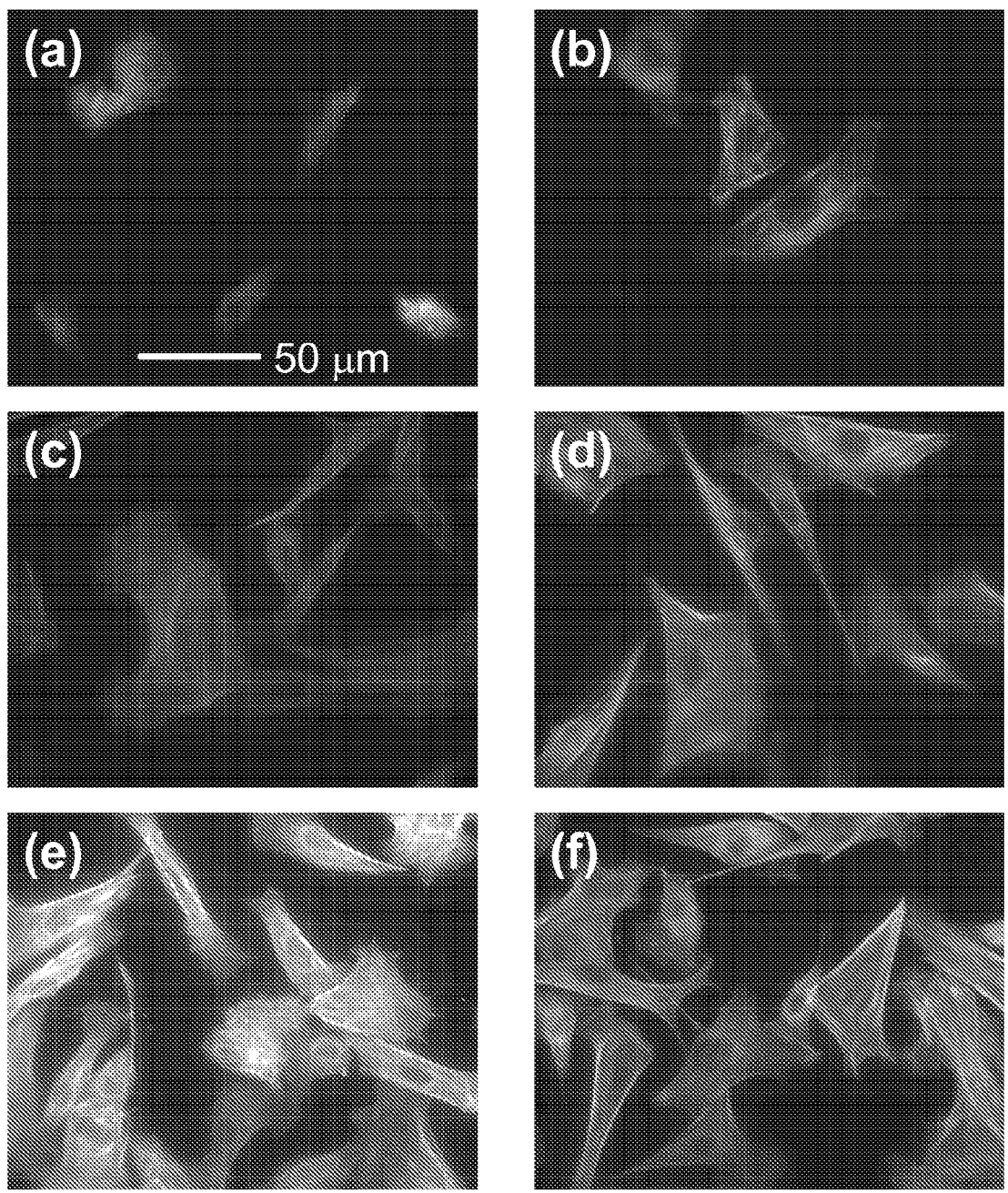
FIG. 4 shows actin cytoskeletons of cells on LDPE surfaces for ion energy fluence equal to (a) 0 $J/m^2$ (untreated), (b) $1.1 \times 10^1$ $J/m^2$, (c) $7.8 \times 10^2$ $J/m^2$, (d) $2.8 \times 10^4$ $J/m^2$, (e) $1.8 \times 10^5$ $J/m^2$, and (f) $6.3 \times 10^5$ $J/m^2$. The cells were seeded in serum-free medium and incubated for 3 h.
Figure 5:
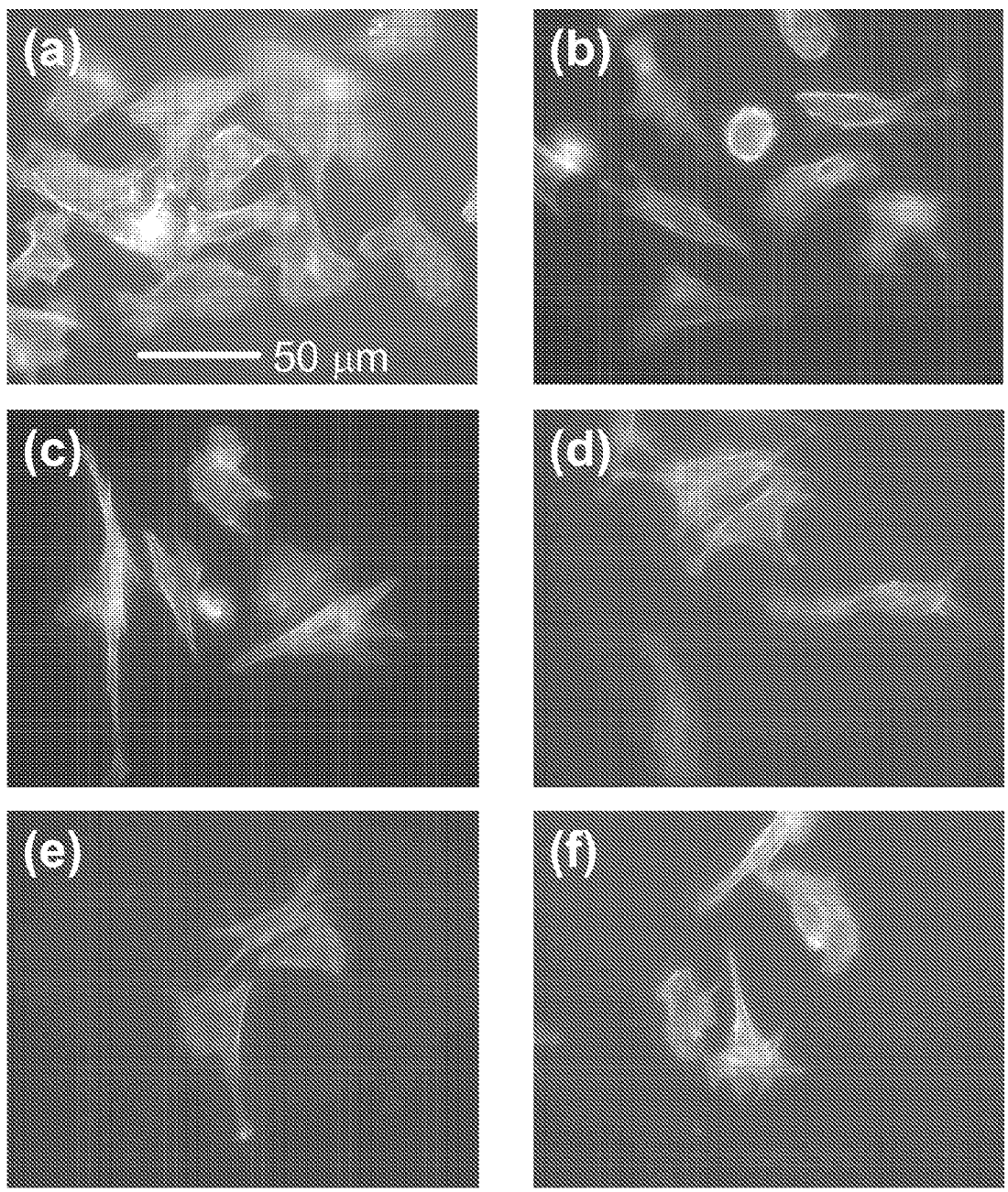
FIG. 5 shows actin cytoskeletons of cells on LDPE surfaces for ion energy fluence equal to (a) 0 $J/m^2$ (untreated), (b) $1.1 \times 10^1$ $J/m^2$, (c) $7.8 \times 10^2$ $J/m^2$, (d) $2.8 \times 10^4$ $J/m^2$, (e) $1.8 \times 10^5$ $J/m^2$, and (f) $6.3 \times 10^5$ $J/m^2$. The cells were seeded and incubated in serum medium for 3 h.

Differences in cell spreading and cytoskeletons were discovered on untreated and plasma-treated LDPE surfaces depending on the ion energy fluence. An enhancement of cell spreading was found for ion energy fluence as low as $1.1 \times 10^1$ J/m² (FIG. 4(b)). While the increase of the ion energy fluence up to $1.8 \times 10^5$ J/m² promoted cell spreading and actin filament assembly in the serum-free medium (FIG. 4), an opposite trend was observed with serum medium (FIG. 5). These results suggest that cell spreading was affected by the presence of different oxygen functionalities only in the serum-free medium. More cell spreading occurred with the increase of oxygen concentration at the surface. It appears that cell spreading was enhanced in the presence of C=O and O=C—OH groups, produced under plasma conditions resulting in ion energy fluence above $10^4$ J/m² (Table 1). A comparison of the cytoskeleton morphologies for serum-free medium and ion energy fluence equal to $1.8 \times 10^5$ J/m² (FIG. 4(e)) and $6.3 \times 10^5$ J/m² (FIG. 4(f)) shows that the modification of the nanoscale morphology (FIGS. 1(c) and 1(d)) did not influence cell spreading. Alternatively, the serum proteins enhanced cell spreading on the hydrophobic (untreated) surface (FIG. 5(a)) and reduced cell spreading on all hydrophilic (plasma-treated) surfaces (FIGS. 5(b)-5(f)). These observations differ from those of previous studies where hydrophilic surfaces were argued to be ideal for cell spreading (Ertel, S. I. et al. *J Biomed Mater Res* 24:1637-1659 (1990)), and suggest that other factors, such as protein adsorption, could play dominant roles in the modification of both hydrophobic and hydrophilic surfaces.

Effect of Incubation Period on Cell Adhesion and Spreading.

To determine the stability and kinetics of cell adhesion, the variation of the normalized cell density with the incubation time was examined for both serum and serum-free media (FIG. 6). For both media, the incubation period did not produce a statistically discernible effect on the cell density of the plasma-treated surfaces. Significantly more cells adhered on the untreated LDPE surface during the 3 h incubation period in the serum medium (FIG. 6(b)) than in the serum-free medium (FIG. 6(a)). However, a profound decrease in cell density was observed after incubation in the serum medium for 24 h. The results shown in FIG. 6(b) suggest that the hydrophobic (untreated) polymer surface initially attracted the cells in the serum medium but could not retain them for a long time, presumably due to degradation and detachment of the adsorbed proteins that resulted in cell removal.

Figure 7:
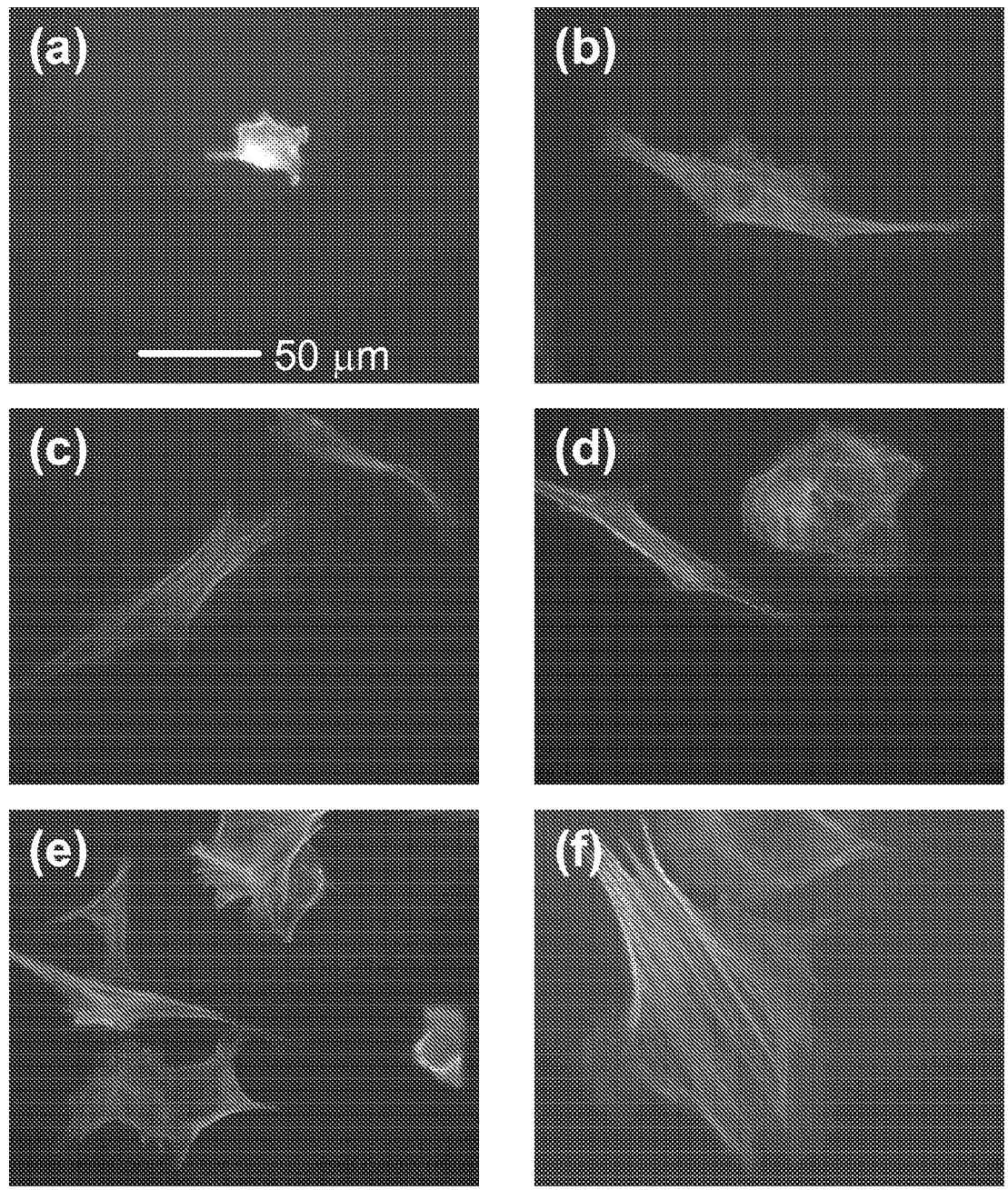
FIG. 7 shows actin cytoskeletons of cells on LDPE surfaces for different ion energy fluence and incubation time and serum-free medium: (a) 0 $J/m^2$ (untreated), 3 h; (b) 0 $J/m^2$ (untreated), 24 h; (c) $7.8 \times 10^2$ $J/m^2$, 3 h; (d) $7.8 \times 10^2$ $J/m^2$, 24 h; (e) $1.8 \times 10^5$ $J/m^2$, 3 h; (f) $1.8 \times 10^5$ $J/m^2$, 24 h.
Figure 8:
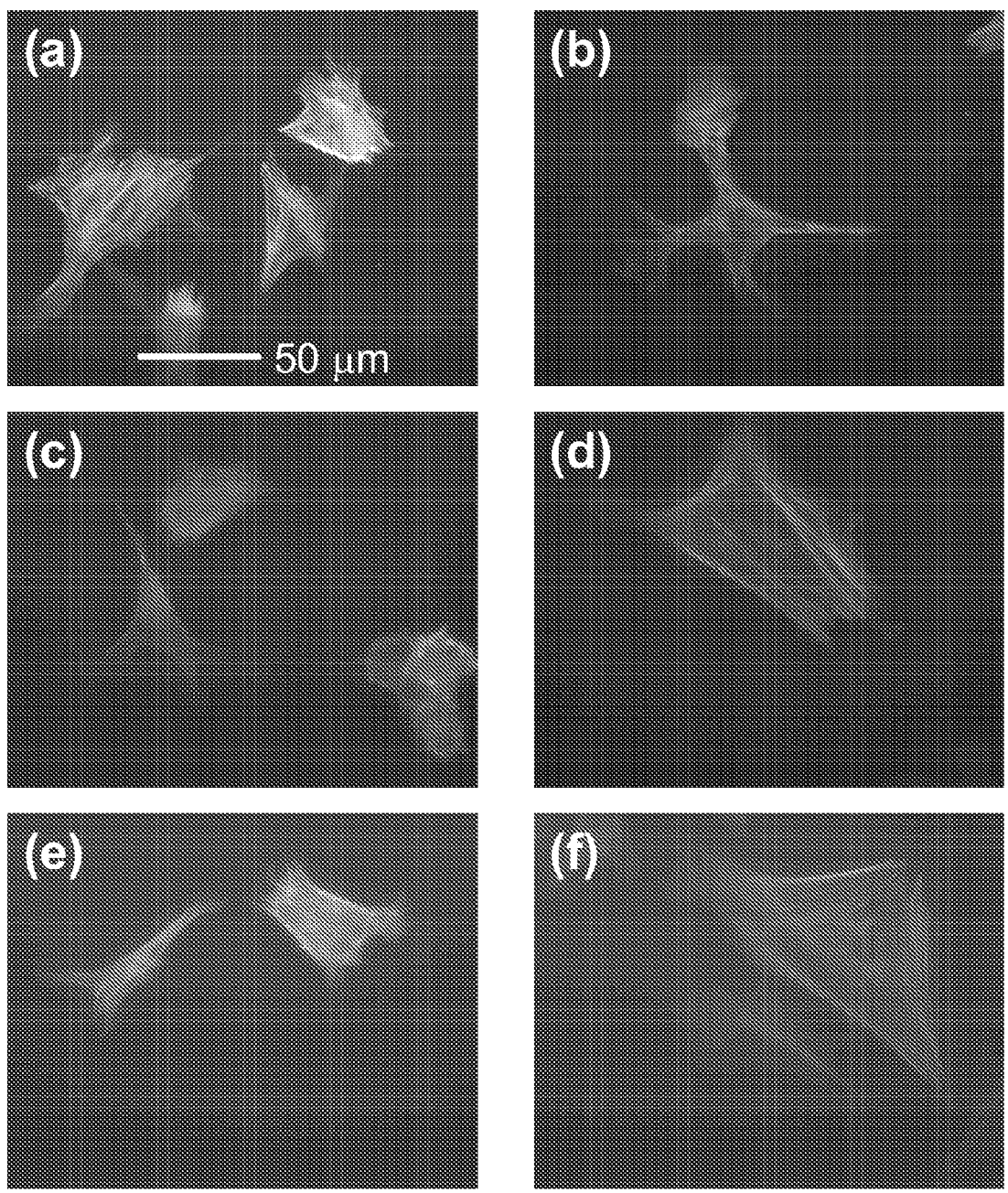
FIG. 8 shows actin cytoskeletons of cells on LDPE surfaces for different ion energy fluence and incubation time and serum medium: (a) 0 $J/m^2$ (untreated), 3 h; (b) 0 $J/m^2$ (untreated), 24 h; (c) $7.8 \times 10^2$ $J/m^2$, 3 h; (d) $7.8 \times 10^2$ $J/m^2$, 24 h; (e) $1.8 \times 10^5$ $J/m^2$, 3 h; (f) $1.8 \times 10^5$ $J/m^2$, 24 h.

The cell spreading behavior demonstrated a dependence on the medium in which the cells were seeded, the incubation time, and the chemical behavior of the LDPE surface. FIG. 7 shows representative results of the cell spreading behavior in the serum-free medium. Cell spreading was more evident on the untreated and plasma-treated surfaces after incubation for 24 h. The cells that adhered on the oxygen-free LDPE surfaces (i.e., untreated and plasma treated for ion energy fluence less than ~$10^2$ J/m²) exhibited elongation by short actin filaments after incubation for 24 h (FIGS. 7(b) and 7(d)). Alternatively, the cells seeded on plasma-treated LDPE surfaces containing oxygen functionalities (ion energy fluence >$10^4$ J/m²) exhibited two-dimensional spreading characterized by long actin filament formation and the establishment of many adhesion points after incubation for 24 h (FIG. 7(f)). Hence, although the number of adhered cells was not affected significantly by the increase of the incubation time from 3 to 24 h, rapid cell adhesion occurred on the hydrophilic surfaces and the cell spreading behavior was influenced by oxygen surface functionalities. FIG. 8 shows a significantly different spreading behavior of the cells seeded in the serum medium. A comparison of the actin cytoskeletons shown in the left column of FIG. 8 with those of the right column indicates that the increase of the incubation time resulted in cell spreading and actin filament assembly on both hydrophobic and hydrophilic polymer surfaces.

Role of Proteins on Cell Adhesion and Spreading.

To examine the interactions of serum proteins and matrix proteins with different surfaces, BAECs were seeded and incubated for 3 h in serum-free medium in the presence of pre-adsorbed BSA, collagen, fibronectin, or a mixture of BSA and fibronectin. BSA has been reported to prevent cell adhesion on polymer surfaces (Grinnell, F. et al., *J Biomed Mater Res* 15:363-381 (1981)). Indeed, very few cells (i.e., ~2-5 on a sample surface area of 0.8 cm$^2$) adhered on both untreated and plasma-treated surfaces with pre-adsorbed BSA; therefore, these results are not included in the normalized cell density plot shown in FIG. 9. The data corresponding to the BSA/fibronectin mixture demonstrate that 1% of BSA completely blocked the cells from adhering on the LDPE surface regardless of the surface chemical modification. On the contrary, collagen yielded a similar adhesion trend with that of the protein-free LDPE, suggesting that the adsorption of collagen on the LDPE surfaces may not be efficient.

In contrast to collagen, pre-adsorbed fibronectin masked the surface modification induced by the Ar plasma treatment, producing indifferent cell adhesion characteristics on the untreated and the plasma-treated LDPE surfaces. The lower cell density of the hydrophilic surface (ion energy fluence of $1.8 \times 10^5$ J/m$^2$) compared to that of the protein-free surface can be attributed to the occupation of the cell adhesion sites by fibronectin molecules. Another plausible explanation is that the conformation of fibronectin on the hydrophilic surfaces may not be optimal for cell adhesion. When both fibronectin and BSA were pre-adsorbed on the polymer surfaces, very few cells adhered on both untreated and plasma-treated (ion energy fluence of $7.8 \times 10^2$ J/m$^2$) LDPE surfaces. However, an increase in cell density was encountered with the increase of the ion energy fluence ($1.8 \times 10^5$ J/m$^2$). Nevertheless, the number of cells adhered on this surface was still less than that of the protein-free surface even though albumin mixed with fibronectin has been reported to produce fibronectin conformation favorable for cell adhesion (Grinnell, F. et al., *J Biol Chem* 257:4888-4893 (1982)). The results shown in FIG. 9 suggest that albumin played a key role in preventing cell adhesion on the less hydrophilic LDPE surface. Because albumin binds strongly to polymer surfaces, it may be inferred that it prevented the attachment of cell-secreted proteins.

Figure 10:
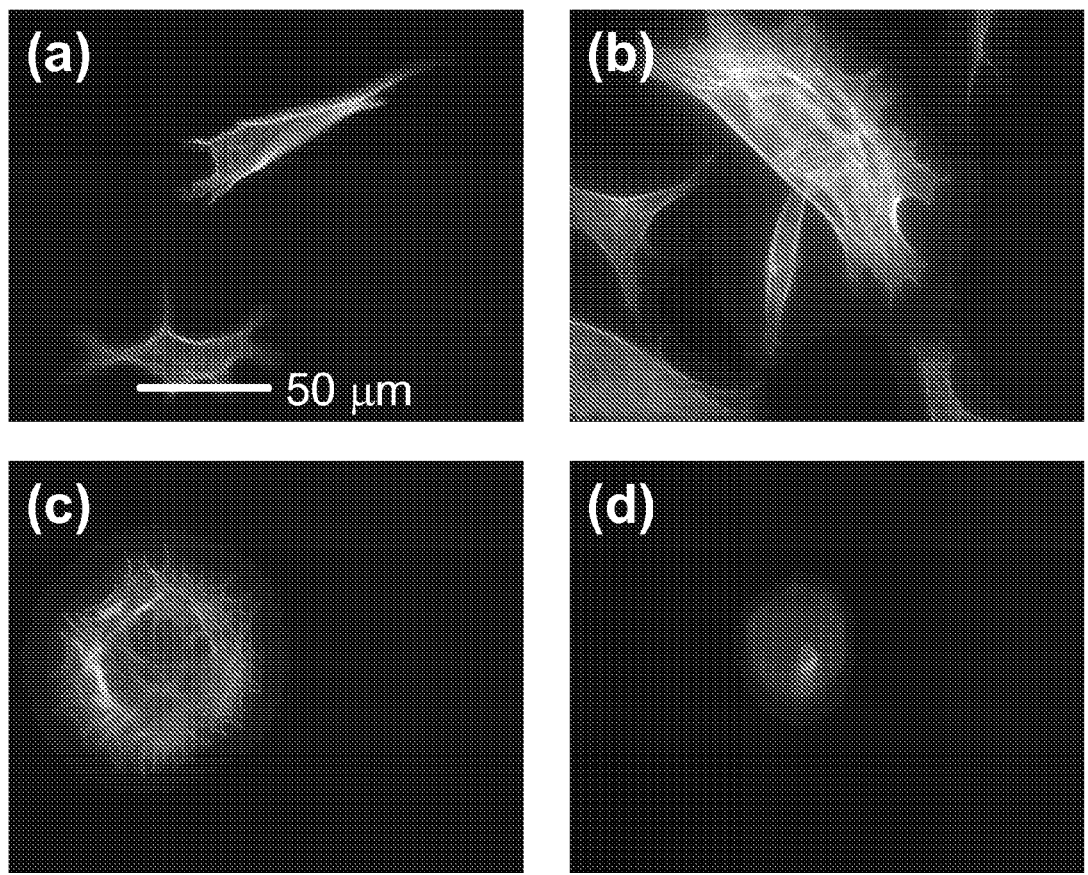
FIG. 10 shows actin cytoskeletons of cells on LDPE surfaces with and without pre-adsorbed proteins and serum-free medium: (a) untreated LDPE without pre-adsorbed proteins, (b) plasma-treated ($1.8 \times 105$ $J/m^2$) LDPE without pre-adsorbed proteins, (c) untreated LDPE with pre-adsorbed fibronectin, and (d) plasma-treated ($1.8 \times 10^5$ $J/m^2$) LDPE with pre-adsorbed BSA and fibronectin.

The cytoskeleton morphologies shown in FIG. 10 demonstrate different cell spreading behaviors on untreated and plasma-treated LDPE surfaces with different pre-adsorbed proteins in serum-free medium. A comparison of the characteristic cell morphologies on the hydrophobic and hydrophilic LDPE surfaces without pre-adsorbed proteins (FIGS. 10(*a*) and 10(*b*), respectively) reveals an enhancement of cell spreading and actin filament assembly on the hydrophilic surface. It was observed that collagen from the serum medium did not affect cell spreading on any of the plasma-treated LDPE surfaces and that cytoskeletons were similar to those shown in FIGS. 10(*a*) and 10(*b*). Significantly different cytoskeleton morphologies were observed in the presence of fibronectin. For example, FIG. 10(*c*) shows that fibronectin promoted cell spreading and actin filament assembly on the untreated hydrophobic surface. This cytoskeleton shape was observed on all the plasma-treated hydrophilic surfaces with pre-adsorbed fibronectin regardless of the surface chemistry modification. Cell spreading decreased significantly and actin filament disappeared in the presence of BSA or BSA/fibronectin mixture (FIG. 10(*d*)), indicating that albumin inhibited cell spreading.

In this study, the adhesion behavior and cytoskeleton morphology of endothelial cells seeded on untreated and Ar plasma-treated LDPE surfaces with different nanotopographies, hydrophilicity (wettability), and oxygen functionalities were examined in serum and serum-free media with and without pre-adsorbed proteins. More cells adhered and spread on plasma-treated surfaces in the serum-free medium than in the serum medium after incubation for 3 h. Increasing the incubation time to 24 h resulted in the detachment of the cells seeded in the serum medium from the untreated hydrophobic surface. However, the increase of the incubation period did not affect cell spreading on the plasma-treated hydrophilic surfaces in both serum and serum-free media. Serum proteins and other pre-adsorbed proteins exhibited different effects on the cell adhesion and spreading characteristics during the 3 h incubation period. In particular, collagen demonstrated a secondary effect on cell adhesion, fibronectin masked the surface chemical modification produced by plasma treatment, and the co-adsorption of albumin and fibronectin inhibited cell adhesion on the hydrophilic plasma-treated surfaces. The results of this investigation demonstrate that Ar plasma treatment is an effective method of enhancing cell adhesion and growth in a serum-free medium for short incubation time and in both serum and serum-free media for long incubation time. These findings illustrate different regulation effects of Ar plasma-induced surface modifications on the endothelial cell behavior and provide insight into complex interactions between cells and proteins at polymer surfaces with different hydrophilicity and type and amounts of oxygen surface functionalities. The results of this investigation are of importance to vascular surface engineering.

Any one or more features of one or more embodiments may be combined with one or more features of any other embodiment without departing from the scope of the invention.

Any recitation of "a", "an" or "the" is intended to mean "one or more" unless specifically indicated to the contrary.

The above description is illustrative but not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

All references, applications, and patents cited above are herein incorporated by reference in their entirety for all purposes. None is admitted to be prior art.

What is claimed is:

1. An article comprising:
    a treated polymeric substrate including:
        a hydrophilic modified surface comprising oxygen functionalities selected from an alkoxide, a carbonyl, an aldehyde, a carboxylate, a carboxyl, and combinations thereof; and
        a bulk region,
            wherein the modified surface has an atomic percentage of oxygen of 13% or more; and
        bioentities on the polymeric substrate.

2. The article of claim 1, wherein the bioentities are cells, and wherein a cell number density on the treated polymeric substrate is increased by at least 50% compared to a cell density on an untreated polymeric substrate.

3. The article of claim 2, wherein the polymeric substrate is configured to contact the bioentities during an incubation period equal to or greater than about 24 hours.

4. The article of claim 1, wherein the bioentities are cells having a cell number density with an initial value on the treated polymeric substrate, and wherein the cell number density is at least 80% of the initial value after a period of time.

5. The article of claim 4, wherein the time period is 24 hours or more.

6. The article of claim 1, wherein the bioentities are cell having a cell number density with an initial value on the treated polymeric substrate, and wherein the cell number density is greater than the initial value after a period of time.

7. The article of claim 6, wherein the time period is 24 hours or more.

8. The article of claim 1, wherein the modified surface has a surface roughness of at least about 5.2 nm and an atomic percentage of oxygen of at least about 13%.

9. The article of claim 1, wherein the modified surface has a surface roughness of 5.2 nm or more.

10. The article of claim 1, wherein the modified surface has a total atomic percentage of the oxygen functionalities of 19% or more.

11. The article of claim 1, wherein the oxygen functionalities comprise a carboxyl group, a carbonyl group or an aldehyde group.

12. The article of claim 1, wherein the substrate comprises polyethylene, polymethylmethacrylate, silicone or polyurethane.

13. The article of claim 1, wherein the substrate has a water contact angle of 60° or less.

14. The article of claim 1, wherein the modified surface is a plasma modified surface.

15. The article of claim 1, wherein the bioentities are adhered to the hydrophilic modified surface of the polymeric substrate.

16. An article comprising:
   (a) a polymeric substrate including:
      (1) a hydrophilic modified surface; and
      (2) a bulk region; and
   (b) bioentities on the polymeric substrate,
   wherein the article is produced by a process comprising:
      (1) contacting a polymeric substrate with an inert plasma, thereby creating the modified surface on the polymeric substrate;
      (2) contacting the modified surface with oxygen, thereby forming oxygen functionalities selected from an alkoxide, a carbonyl, an aldehyde, a carboxylate, a carboxyl, and combinations thereof on the modified surface;
   and
      (3) depositing the bioentities on the polymeric substrate.

17. The article of claim 16, wherein the modified surface has an atomic percentage of oxygen of 13% or more.

18. The article of claim 16, wherein the modified surface has a surface roughness of 5.2 nm or more.

19. The article of claim 16, wherein the bioentities are cells having a cell number density with an initial value on the polymeric substrate, and wherein the cell number density is at least 80% of the initial value after a period of time.

20. The article of claim 16, wherein the substrate has a water contact angle of 60° or less.

* * * * *